US010690538B2

(12) United States Patent
Lin

(10) Patent No.: US 10,690,538 B2
(45) Date of Patent: Jun. 23, 2020

(54) OPTICAL SENSOR MODULE AND A WEARABLE DEVICE INCLUDING THE SAME

(71) Applicants: LITE-ON OPTO TECHNOLOGY (CHANGZHOU) CO., LTD., Jiangsu Province (CN); LITE-ON TECHNOLOGY CORP., Taipei (TW)

(72) Inventor: Chen-Hsiu Lin, Taipei (TW)

(73) Assignees: LITE-ON OPTO TECHNOLOGY (CHANGZHOU) CO., LTD., Jiangsu Province (CN); LITE-ON TECHNOLOGY CORP., Taipei (TW)

( * ) Notice: Subject to any disclaimer, the term of this patent is extended or adjusted under 35 U.S.C. 154(b) by 438 days.

(21) Appl. No.: 15/434,298

(22) Filed: Feb. 16, 2017

(65) Prior Publication Data
US 2017/0241834 A1    Aug. 24, 2017

(30) Foreign Application Priority Data

Feb. 19, 2016    (CN) .......................... 2016 1 0094449

(51) Int. Cl.
| A61B 5/02 | (2006.01) |
| A61B 5/024 | (2006.01) |
| A61B 5/1455 | (2006.01) |
| H01L 31/0232 | (2014.01) |
| H01L 31/12 | (2006.01) |
| G01J 1/02 | (2006.01) |
| G01J 1/04 | (2006.01) |
| G01J 1/06 | (2006.01) |
| G01J 1/42 | (2006.01) |
| A61B 5/00 | (2006.01) |
| H01L 25/16 | (2006.01) |

(52) U.S. Cl.
CPC .............. G01J 1/42 (2013.01); A61B 5/0059 (2013.01); A61B 5/14552 (2013.01); G01J 1/0271 (2013.01); G01J 1/0407 (2013.01); G01J 1/06 (2013.01); A61B 5/02416 (2013.01); A61B 5/02438 (2013.01); A61B 5/681 (2013.01); G01J 2001/0257 (2013.01); H01L 25/167 (2013.01); H01L 31/0232 (2013.01)

(58) Field of Classification Search
CPC .... G01J 1/42; G01J 1/06; G01J 1/0271; G01J 1/0407; A61B 5/0059; A61B 5/681
USPC ........................................................ 600/476
See application file for complete search history.

(56) References Cited

U.S. PATENT DOCUMENTS

| 4,114,177 A * | 9/1978 | King ....................... H01L 31/16 |
| | | 250/551 |
| 2010/0302745 A1* | 12/2010 | Hsu .......................... H05K 3/32 |
| | | 361/749 |

(Continued)

*Primary Examiner* — Patricia J Park
*Assistant Examiner* — Victoria Fang
(74) *Attorney, Agent, or Firm* — Rosenberg, Klein & Lee

(57) ABSTRACT

An optical sensor module includes a support unit, a light-receiving unit and a light-emitting unit. The support unit includes a main plate, and a side plate inclined relative to the main plate. The light-receiving unit includes a photodetector disposed on the main plate and having a light-receiving surface located away from the main plate, and a light-blocking member covering part of the photodetector. The light-emitting unit emits light toward an imaginary line perpendicular to the light-receiving surface, and is disposed on the side plate. A wearable device including the optical sensor is also disclosed.

19 Claims, 10 Drawing Sheets

(56) References Cited

U.S. PATENT DOCUMENTS

| | | | |
|---|---|---|---|
| 2014/0275850 A1* | 9/2014 | Venkatraman | A61B 5/0002 600/301 |
| 2015/0238125 A1* | 8/2015 | Acosta | A61B 5/0071 600/310 |
| 2016/0022210 A1* | 1/2016 | Nuovo | A61B 5/681 600/301 |
| 2016/0029911 A1* | 2/2016 | Lee | A61B 5/02427 600/301 |
| 2016/0282149 A1* | 9/2016 | Oguchi | G01D 5/3473 |
| 2016/0345881 A1* | 12/2016 | Sarantos | A61B 5/14552 |

* cited by examiner

OPTICAL SENSOR MODULE AND A WEARABLE DEVICE INCLUDING THE SAME

CROSS-REFERENCE TO RELATED APPLICATION

This application claims priority to Chinese Invention Patent Application No. 201610094449.8, filed on Feb. 19, 2016.

FIELD

The disclosure relates to a sensor module and a wearable device having the sensor module, and more particularly to an optical sensor module and a wearable device having the optical sensor module.

BACKGROUND

Generally, a wearable device for monitoring personal biological data has a light-emitting member and a photodetector disposed on a same plane. However, light rays emitted from the light-emitting member and reflected by the user's skin may not be effectively detected and correctly analyzed by the photodetector.

SUMMARY

Therefore, an object of the present disclosure is to provide an optical sensor module that can enhance light collection efficiency and a wearable device including the optical sensor module.

Accordingly, an optical sensor module of the present disclosure has a support unit, a light-receiving unit and at least one light-emitting unit. The support unit includes a main plate and at least one side plate inclined relative to the main plate. The light-receiving unit includes a photodetector that is disposed on a top of the main plate and that has a light-receiving surface located away from the main plate, and a first light-blocking member that surrounds the photodetector. The at least one light-emitting unit is disposed on the at least one side plate, and includes at least one light source that has a light-emitting surface. The optical sensor module defines an imaginary line perpendicular to the light-receiving surface. The at least one light source emits light toward the imaginary line.

The advantages of the disclosure reside in that, through the side plates being inclined relative to the main plate, the light-receiving unit and the light-emitting units are disposed on different planes such that the light, which is emitted from the light-emitting units and reflected by the user's skin, can effectively enter the light-receiving unit, thereby increasing the measurement efficiency and accuracy of the optical sensor module.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
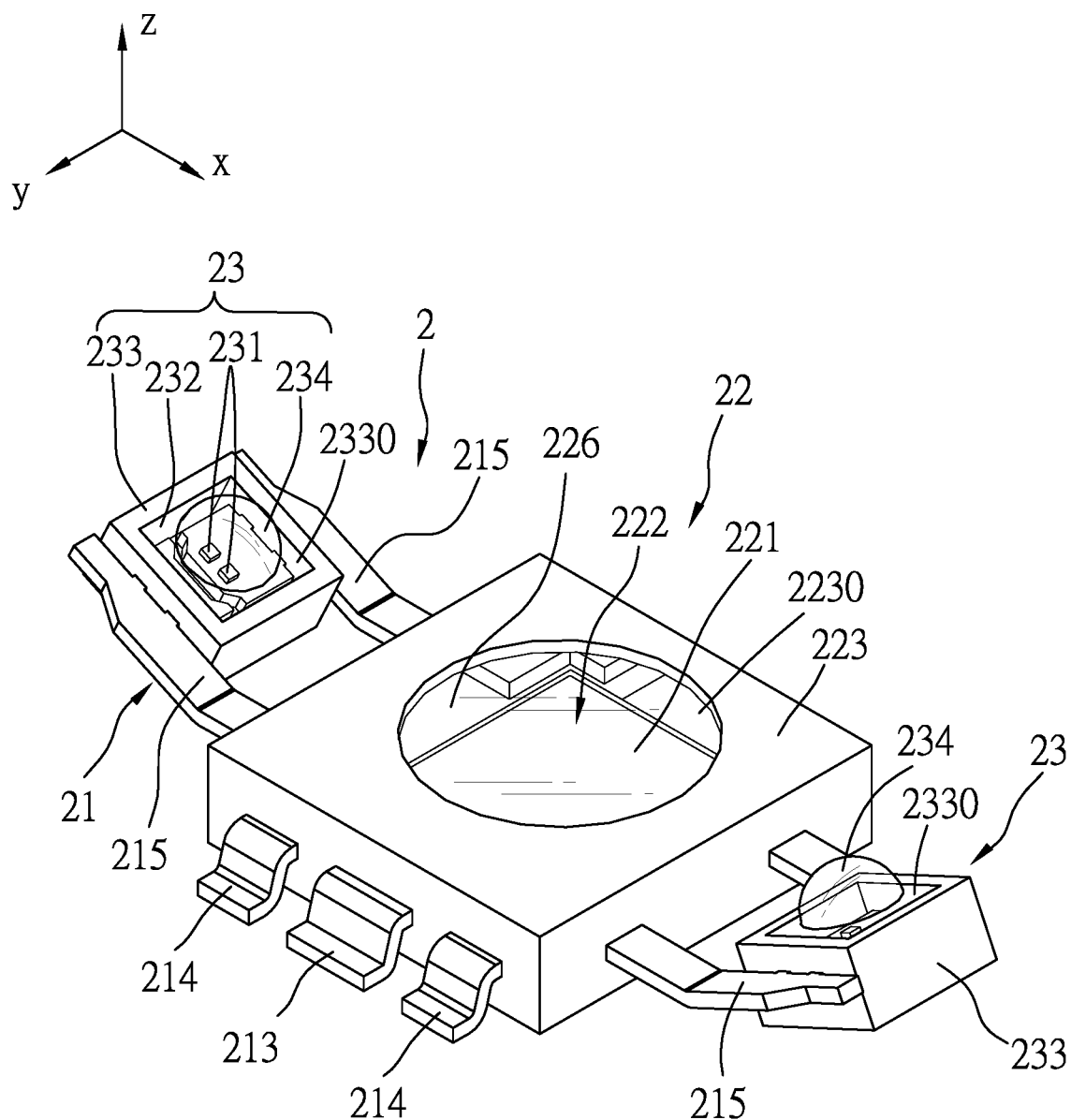
FIG. 1 is a perspective view of an optical sensor module of an embodiment according to the present disclosure.
Figure 2:
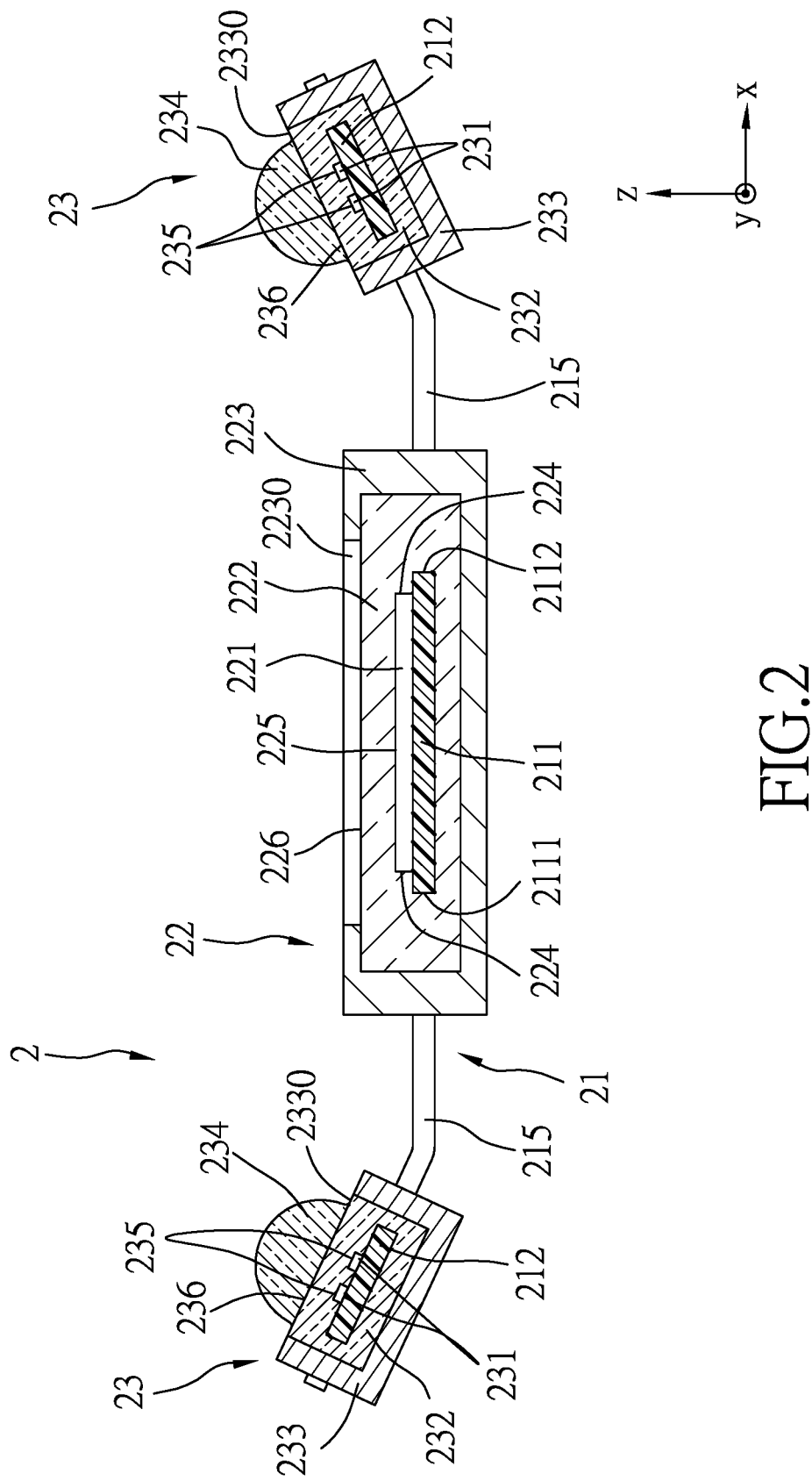
FIG. 2 is a sectional view of the embodiment.
Figure 3A:
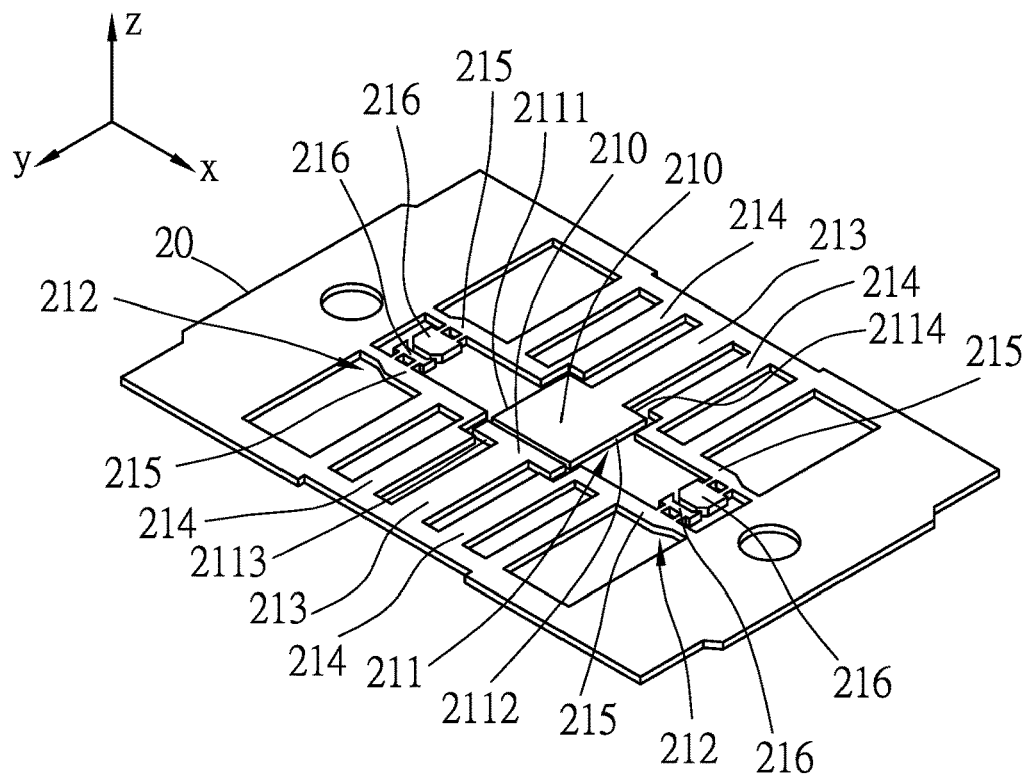
FIGS. 3A to 3E illustrate consecutive steps of an exemplified method of forming the optical sensor module of the embodiment.

Referring to FIGS. 1, 2 and 3A, an optical sensor module 2 according to an embodiment of the present disclosure includes a light-receiving unit 22, two light-emitting units 23 disposed opposite to each other with respect to the light-receiving unit 22, and a support unit 21 connecting the light-receiving unit 22 and the light-emitting units 23.

The support unit 21 includes a main plate 211 that has first and second sides 2111, 2112 that are opposite to each other, and two side plates 212 that are respectively disposed adjacent to the first and second sides 2111, 2112 of the main plate 211 and inclined relative to the main plate 211. The main plate 211 further has third and fourth sides 2113, 2114 that are opposite to each other and that respectively interconnect the first and second sides 2111, 2112. The main plate 211 further includes two spaced-apart first leg portions 213 that respectively extend from the third and fourth sides 2113, 2114 in a lengthwise direction (Y) to be away from each other. Each of the side plates 212 includes two bridge portions 215 that separately extend toward the main plate 211 in an extending direction (X) transverse to the lengthwise direction (Y), and two spaced-apart second leg portions 214 that are respectively connected to the bridge portions 215 and that are opposite from each other in the lengthwise direction (Y). Each of the first leg portions 213 of the main plate 211 is parallel to and electrically isolated from a corresponding one of the second leg portions 214 of the side plate 212.

Specifically, the support unit 21 is formed on a single metal plate, and the bridge portions 215 of each of the side plates 212 are bendable relative to the main plate 211 in an elevational direction (Z) transverse to both the lengthwise direction (Y) and the extending direction (X) such that the side plates 212 and the main plate 211 are formable into a three dimensional (3D) U-shaped or V-shaped structure for converging light. In this embodiment, the metal plate for forming the support unit 21 is exemplified to be made from a copper material with relatively good heat-dissipation and plasticity properties, but is not limited thereto.

The light-receiving unit 22 includes a photodetector 221 disposed on a top of the main plate 211, a light-transmissible member 222 and a first light-blocking member 223. The photodetector 221 includes two opposite side surfaces 224 that respectively and spacedly face the side plates 212, and a light-receiving surface 225 that connects the side surfaces 224 and that is located away from the main plate 211. The light-receiving surface 225 is adapted for receiving light signals to be analyzed. The light-transmissible member 222 encapsulates the photodetector 221, and has a top surface 226 located away from the light-receiving surface 225. The first light-blocking member 223 surrounds the light-transmissible member 222 and exposes the top surface 226 of the light-transmissible member 222 therefrom.

In this embodiment, the optical sensor module 2 may be applied for measuring personal biological information. Thus, the photodetector 221 may be configured to receive and detect photoplethysmography signals.

In detail, the bridge portions 215 of the side plates 212 extend toward the first and second sides 2111, 2112 of the main plate 211 in the extending direction (X), respectively, and are exposed from and inclined relative to the first light-blocking member 223. The light-transmissible member 222 encapsulates not only the photodetector 221 but also the main plate 211 in a manner that the first and second leg portions 213, 214 extend outwardly of the light-transmissible member 222 and are exposed outwardly of two opposite ends of the first light-blocking member 223 so as to provide external electrical connections. Further, the first light-blocking member 223 has an opening 2230 that is registered with the light-receiving surface 225, such that the top surface 226 of the light-transmissible member 222 is partially exposed from the opening 2230. For example, a circular or quadrangular shape with round corners is preferredly used in the opening 2230. The shape and size of the opening 2230 will be dependent on the photodetector 221. By virtue of the first light-blocking member 223 partially exposing the top surface 226 of the light-transmissible member 222, light rays directly emitted from the light-emitting units 23 are prevented from being received by the photodetector 221 to affect a measurement result.

The light-emitting units 23 are respectively disposed on the side plates 212 and are symmetrical to each other with respect to the photodetector 221. In this embodiment, each of the light-emitting units 23 is exemplified to include two light sources 231 mounted on the side plates 212, respectively, a light-transmissible encapsulant 232, a second light-blocking member 233, and a lens 234 disposed on the light-transmissible encapsulant 232.

Each of the light sources 231 has a light-emitting surface 235 located away from a respective one of the side plates 212. The light-transmissible encapsulant 232 encapsulates the light-emitting sources 231, and has a top surface 236 located away from the light-emitting surfaces 235 of the light sources 231. The second light-blocking member 233 surrounds the light-transmissible encapsulant 232 and the light-emitting sources 231, and has an aperture 2330 registered with the light-emitting surfaces 235 of the light-emitting sources 231. The top surface 236 of the light-transmissible encapsulant 232 is exposed from the aperture 2330 such that the light rays emitted from the light-emitting sources 231 can exit through the top surface 236. The lens 234 is disposed on the top surface 236, thereby enhancing luminous efficiency of the light-emitting sources 231.

It should be noted that the number and luminous color of the light-emitting sources 231 are not limited to that disclosed herein and can be adjusted based on practical application. In this embodiment, in order to obtain accurate personal biological information, the two light sources 231 of each of the light-emitting units 23 are respectively arranged to emit green light having a wavelength between 520 nm and 535 nm, and orange light having a wavelength between 587 nm and 597 nm, so that the optical sensor module 2 can use light emitted from the light sources 231 to measure the personal biological information.

Further, the first and second light-blocking members 223, 233 may be selectively made from a light-absorbing material, such as a dark resin material or a black matrix (BM) resist material, but is not limited thereto. The light-absorbing materials used for making the first and second light-blocking members 223, 233 may be the same or different as long as the first and second light-blocking members 223, 233 can isolate and absorb light effectively. The light-transmissible member 222 and the light-transmissible encapsulant 232 are made from a light-transmissible material, such as an epoxy resin material, an acrylic resin material, etc. The light-transmissible materials used for making the light-transmissible member 222 and the light-transmissible encapsulant 232 may be the same or different. In this embodiment, the light-transmissible member 222 and the light-transmissible encapsulant 232 are exemplified to be made from an epoxy resin material.

It should be noted that the first leg portions 213 are electrically connected to the photodetector 221, and the second leg portions 214 of each of the side plates 212 are electrically connected to the light sources 231 mounted thereon. Since the first leg portions 213 are electrically isolated from the second leg portions 214, the electrical connection of the first leg portions 213 and the photodetector 221 are controllable independently from the electrical connection of the second leg portions 214 and the light sources 231 for each of the side plates 212, so that a circuit layout for application of the optical sensor module 2 to other devices can be simplified.

FIGS. 3A to 3E illustrate the process for forming the optical sensor module 2 according to the present disclosure.

As shown in FIG. 3A, a copper plate 20 is formed into the support unit 21. Specifically, the main plate 211 includes two spaced-apart main portions 210 opposite to and spaced apart from each other in the lengthwise direction (Y), and the spaced-apart main portions 210 cooperatively define the first and second sides 2111, 2112 of the main plate 211 in the lengthwise direction (Y). Each of the two main portions 210 has an extending side interconnecting the first and second sides 2111, 2112. The extending sides of the two main portions 210 are opposite to and distant from each other and serve as the third and fourth sides 2113, 2114. In other words, the first leg portions 213 respectively and oppositely extend from the extending sides of the main portions 210 in the lengthwise direction (Y). Each of the side plates 212 that are respectively located from the first and second sides 2111, 2112 of the main portions 210 includes two spaced-apart body portions 216 that are opposite to each other in the lengthwise direction (Y). The bridge portions 215 of each of the side plates 212 are respectively connected to the body portions 216 and extend toward the main portions 210 in the extending direction (X), and the bridge portions 215 of each of the side plates 212 are disconnected from the main portions 210. Further, the second leg portions 214 of each of the side plates 212 are respectively connected to and extend from ends of the bridge portions 215 in the lengthwise direction (Y). Each of the first leg portions 213 of the main portions 210 of the main plate 211 is parallel to and electrically disconnected from a corresponding one of the second leg portions 214 of the body portions 216 of the side plate 212. In order to conform to the shapes of the main portions 210, each of the bridge portions 215 of each of the side plates 212 is formed with a cut-off 217 at the end that the corresponding second leg portion 214 extends from and intersects therewith so as to receive a corner portion of the corresponding main portion 210. In this way, a sufficient space for receiving the photodetector 221 is provided.

Figure 3B:
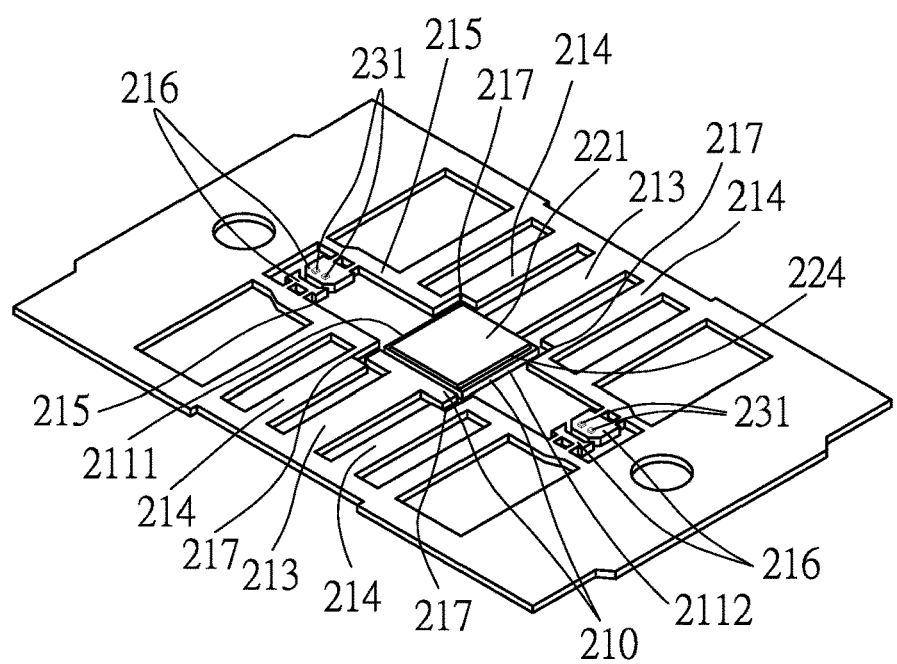

As shown in FIG. 3B, the photodetector 221 is disposed on and electrically connected to one of the main portions 210, and the two light sources 231 of each of the light-emitting units 23 are disposed on and electrically connected to one of the body portions 216 of a respective one of the side plates 212.

Figure 3C:
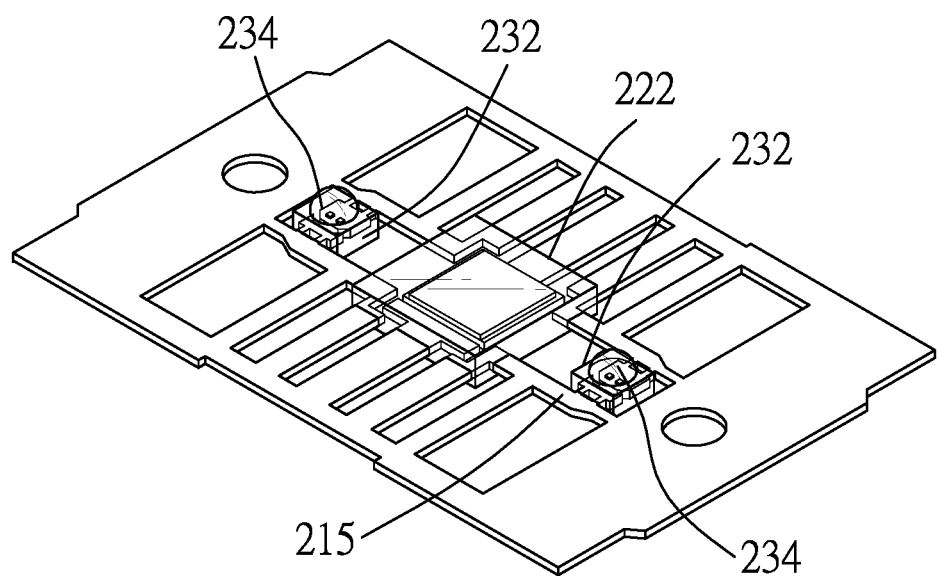
Figure 3D:
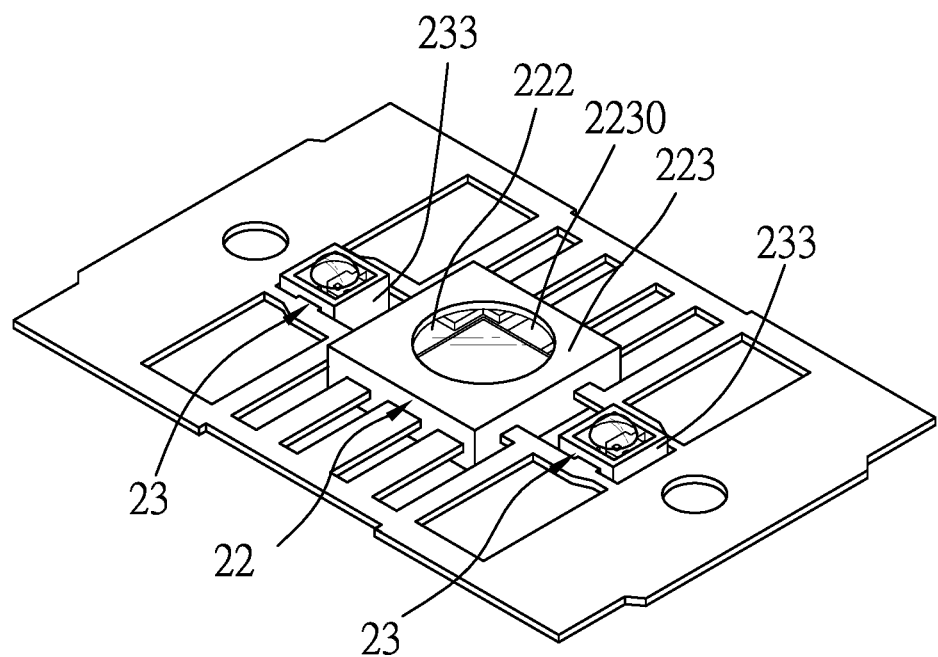

As shown in FIGS. 3C and 3D, the light-transmissible member 222 is formed to encapsulate the photodetector 221, the main portions 210, parts of the bridge portions 215 of each of the side plates 212, parts of the first leg portions 213 of the main plate 211 and parts of the second leg portions 214 of each of the side plates 212. For each of the light-emitting units 23, the light-transmissible encapsulant 232 is formed to encapsulate the light-emitting sources 231 and the body portions 216 of the corresponding side plates 212, and the lens 234 is disposed on the light-transmissible encapsulant 232. Thereafter, the first light-blocking member 223 is formed to surround the light-transmissible member 222, and the second light-blocking members 233 are formed to surround the light-transmissible encapsulants 232, respectively, thereby completing the forming of the light-receiving units 22 and the light-emitting units 23. It should be noted that the lens 234 can be molded in a one-piece form with the light-transmissible encapsulant 232.

Figure 3E:
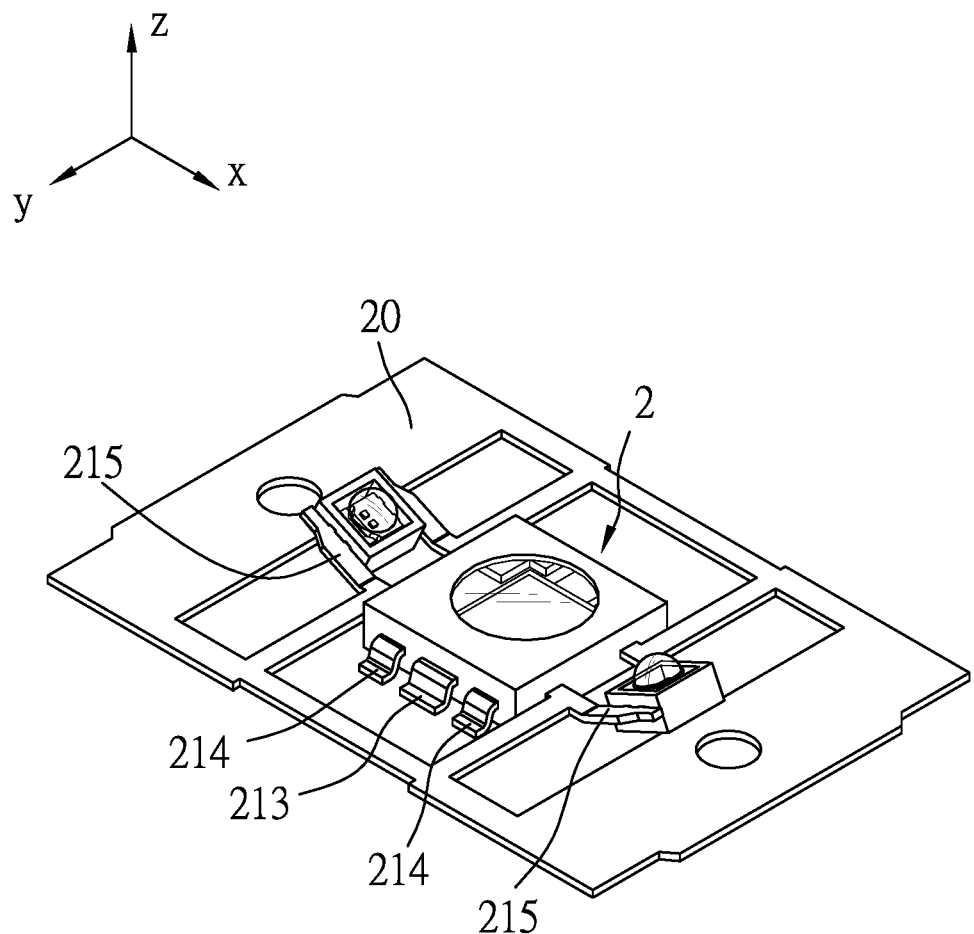

As shown in FIG. 3E, since the support unit 21 is made from the single copperplate 20 with good plasticity, the bridge portions 215 may be bent toward the light-receiving unit 22 and lifted in the elevational direction (Z) so as to make the body portions 216 of each of the side plates 212 angularly inclined with respect to the main plate 211. In one form, when the light sources 231 of one of the light-emitting units 23 are the same as those of the other of the light-emitting units 23, the bridge portions 215 of the two side plates 212 are bent at the same angle relative to the main plate 211. Afterwards, the first leg portions 213 and the second leg portions 214 of the side plates 212 are bent and partially cut off from the copper plate 20, and unnecessary parts of the copper plate 20 are subsequently cut and removed from the support unit 21, thereby forming the optical sensor module 2 (See FIG. 1).

Figure 4:
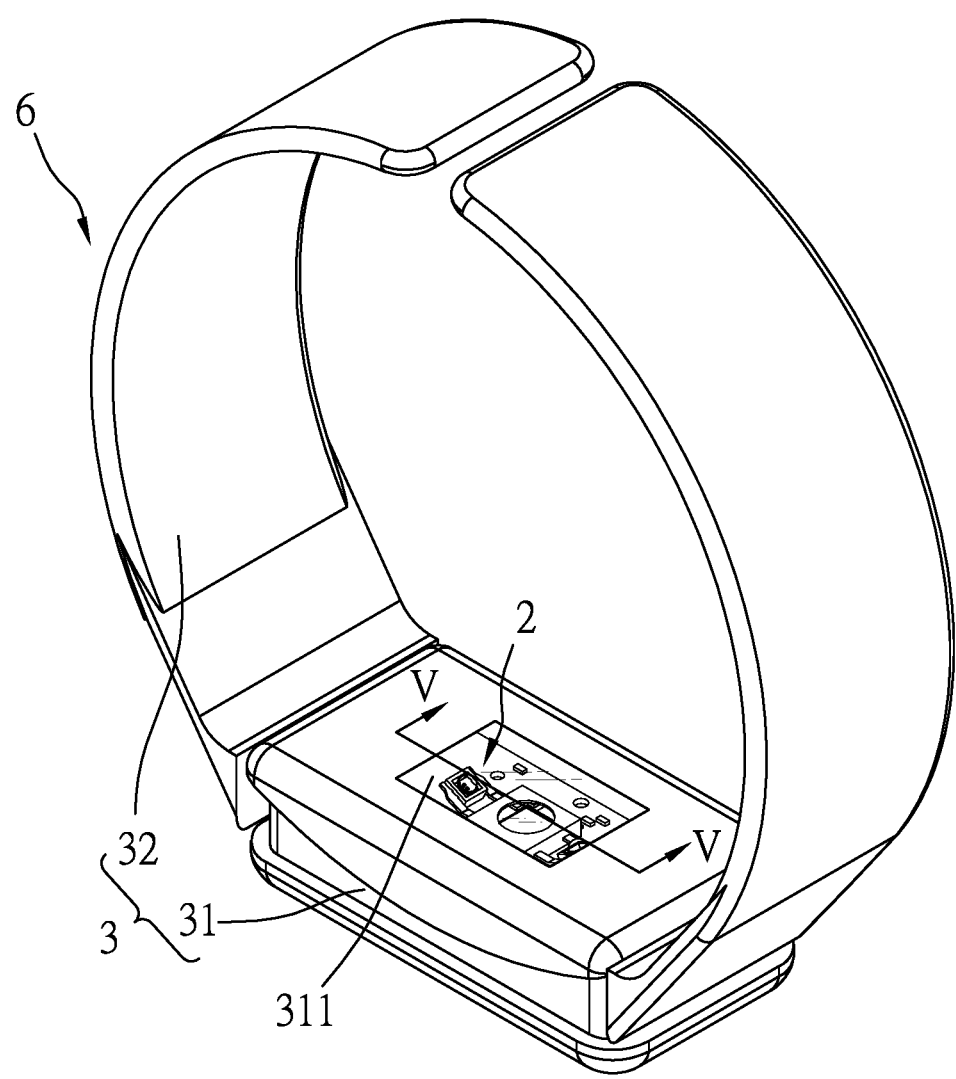
FIG. 4 is a perspective view of an embodiment of a wearable device including the optical sensor module according to the present disclosure.
Figure 5:
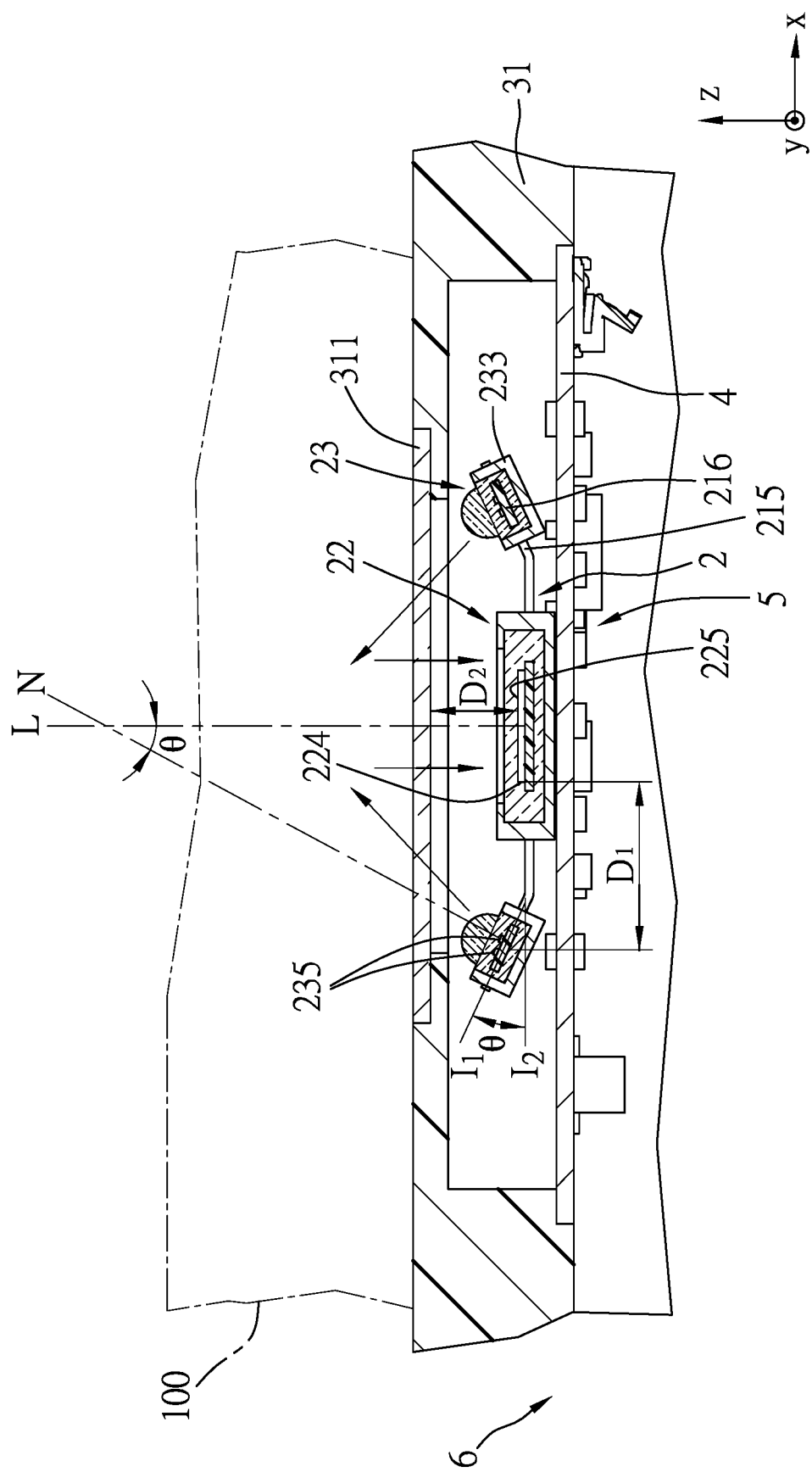
FIG. 5 is a sectional view taken along the line V-V of FIG. 4.

Referring to FIGS. 4 and 5, the aforesaid optical sensor module 2 may be applied to and included in a wearable device 6 according to the present disclosure. The wearable device 6 can be worn by a user and contact the user's skin 100 for measuring photoplethysmography (PPG) signals from the user. The wearable device 6 includes a housing 3, a circuit board 4 disposed in the housing 3, the optical sensor module 2 mounted on the circuit board 4, and a processor unit 5 mounted on the circuit board 4 and electrically connected to the optical sensor module 2.

The housing 3 includes a housing body 31 that has a transparent cover 311 for contacting with the user's skin 100, and a wearing member 32 connected to the housing body 31 and configured to be worn by the user. The configurations of the housing body 31 and the wearing member 32 are not limited to those disclosed herein. In this embodiment, the design of the housing 3 is exemplified to be in a form of a watch or a bracelet. The wearing member 32 is curvedly connected to two opposite ends of the housing body 31 for being able to be worn on the user's wrist.

The circuit board 4 is disposed in the housing body 31. The connection of the circuit board 4 and the housing body 31 is not especially limited as long as the circuit board 4 is stably positioned inside the housing body 31. In order to achieve a better effect, the circuit board 4 is positioned inside the housing body 31 in parallel with the transparent cover 311.

When the optical sensor module 2 is applied to the wearable device 6, the optical sensor module 2 is located between the transparent cover 311 and the circuit board 4 through electrical connection of the first and second leg portions 213, 214 to a surface of the circuit board 4. Further, through the connection arrangement of the first and second leg portions 213, 214 and the circuit board 4, a distance between the light-receiving unit 22 and the transparent cover 311 is adjustable to achieve optimized reflection and reception effects. The processor unit 5 is disposed on the circuit board 4 oppositely to the optical sensor module 2 and is electrically connected to the first and second leg portions 213, 214 of the optical sensor module 2. Electronic components may be mounted on upper and lower surfaces of the circuit boards 4 through the surface mount technology (SMT), thereby reducing layers of the circuit board 4. Further, since each of the light-emitting units 23 together with the corresponding side plate 212 are lifted in the elevational direction (Z) by bending the bridge portions 215 of the corresponding side plate 212 in the elevational direction (Z) toward the light-receiving unit 22, the light-emitting units 23, the side plates 212 and the circuit board 4 cooperate with each other to define a space to receive the electronic components intended to be mounted on the circuit board 4, thereby reducing the size of the wearable device 6.

It should be noted that the position and the inclined angle of each of the light-emitting units 23 with respect to the light-receiving unit 22 are predetermined in order to optimize the effects of the optical sensor module 2.

In one implementation, the optical sensor module 2 defines an imaginary line (L) perpendicular to the light-receiving surface 225 and extending in the elevational direction (Z). Each of the light-emitting units 23 has a geometric center and defines a normal line (N) normal to the light-emitting surface 235 of one of the light sources 231, such that an included angle (θ) is formed between the normal line (N) and the imaginary line (L). On the other hand, for each of the side plates 212, one of the body portions 216, on which the light sources 231 of a respective one of the light-emitting units 23 are disposed, defines an imaginary lengthening line ($I_1$) extending therethrough and normal to the normal line (N), and the optical sensor module 2 further defines an imaginary extending line ($I_2$) extending through the light-receiving unit 22 in the extending direction (X) and normal to the imaginary line (L), such that an included angle between the imaginary lengthening line ($I_1$) and the imaginary extending line ($I_2$) is equal to θ. In addition, $D_1$ denotes a distance between the geometric center of each of the light-emitting units 23 and a respective one of the side surfaces 224 of the photodetector 221, and $D_2$ represents a distance between the light-receiving surface 225 and the transparent cover 311; these parameters $D_2$, θ and $D_1$ satisfy the inequality of D2 tan θ<D1/2.

Furthermore, regarding subsequent applications, a space for containing the optical sensor module 2 is predetermined by defining an outer predetermined reflection surface, so that a distance is formed between the light-receiving surface 225 and the outer predetermined reflection surface to decide the bent angle of the bridge portions 215.

Alternatively, the optical sensor module 2 can be packaged in a package body (not shown), such as a light-transmissible encapsulant, that has an inner surface facing the light-receiving surface 225 of the photodetector 221, and the transparent cover 311 can be omitted. In this case, $D_2$ represents a distance between the light-receiving surface 225 and the inner surface of the package body to satisfy $D_2$ tan θ<$D_1$/2.

Since the included angle (θ) is formed between the light-receiving unit 22 and each of the light-emitting units 23, the light-receiving unit 22 and the light-emitting units 23 are structurally arranged in the three dimensional manner, such that the light sources 231 of each of the light-emitting units 23 are inclined relative to the light-receiving unit 22 and have light inclination angles, thereby emitting light toward the imaginary line (L) to reduce total reflection caused by the transparent cover 311 or the inner surface of the package body when the transparent cover 311 is omitted. Through the foregoing configuration, the light emitted from the light sources 231 of the light-emitting units 23 is more directed toward the user. Further, by virtue of each of the light-emitting units 23 having the structural arrangement of the second light-blocking member 233 and the lens 234, the light emitted from the light sources 231 is enhanced in brightness and is collected effectively and distributed directly toward the user's skin 100.

When the light sources 231 emit light to the user, the light is reflected from the user's skin 100 toward the light-receiving surface 225, and is received by the photodetector 221. With further reference to FIGS. 1 and 5, because the light-transmissible member 222 encapsulates the photodetector 221 and is surrounded by the first light-blocking member 223, interference of the light rays, which are directly emitted from the light-emitting member and not reflected by the user's skin, with the photodetector can be avoided. The photodetector 221 is able to receive a majority of the light reflected from the user's skin 100 through the top surface 226 of the light-transmissible member 222. Therefore, the photodetector 221 can more effectively receive the light reflected from the user's skin 100. Further, by virtue of the limitation of the inequality of $D_2 \tan \theta < D_1/2$, an improper distance between the light-receiving unit 22 and each of the light-emitting units 23 is prevented from causing the photodetector 221 to insufficiently receive the light reflected from the user's skin 100, and the light emitted from the light sources 231 is prevented from being reflected by the transparent cover 311 or by the inner surface of the package body when the transparent cover 311 is omitted.

In summary, because each of the side plates 212 is inclined relative to the main plate 211, and because the included angle (θ) is formed between the normal line (N) defined by each of the light-emitting units 23 and the imaginary line (L) defined by the optical sensor module 2, the light-receiving unit 22 and the light-emitting units 23 are structurally arranged in the three dimensional manner, such that the light emitted from the light-emitting units 23 and reflected from the user's skin 100 can be effectively received by the photodetector 221, thereby increasing the measurement efficiency and accuracy of the optical sensor module 2. In addition, satisfying $D_2 \tan \theta < D_1/2$ prevents the light emitted from the light-emitting sources 231 from being reflected by the transparent cover 311 or by the inner surface of the package body when the transparent cover 311 is omitted.

Figure 6:
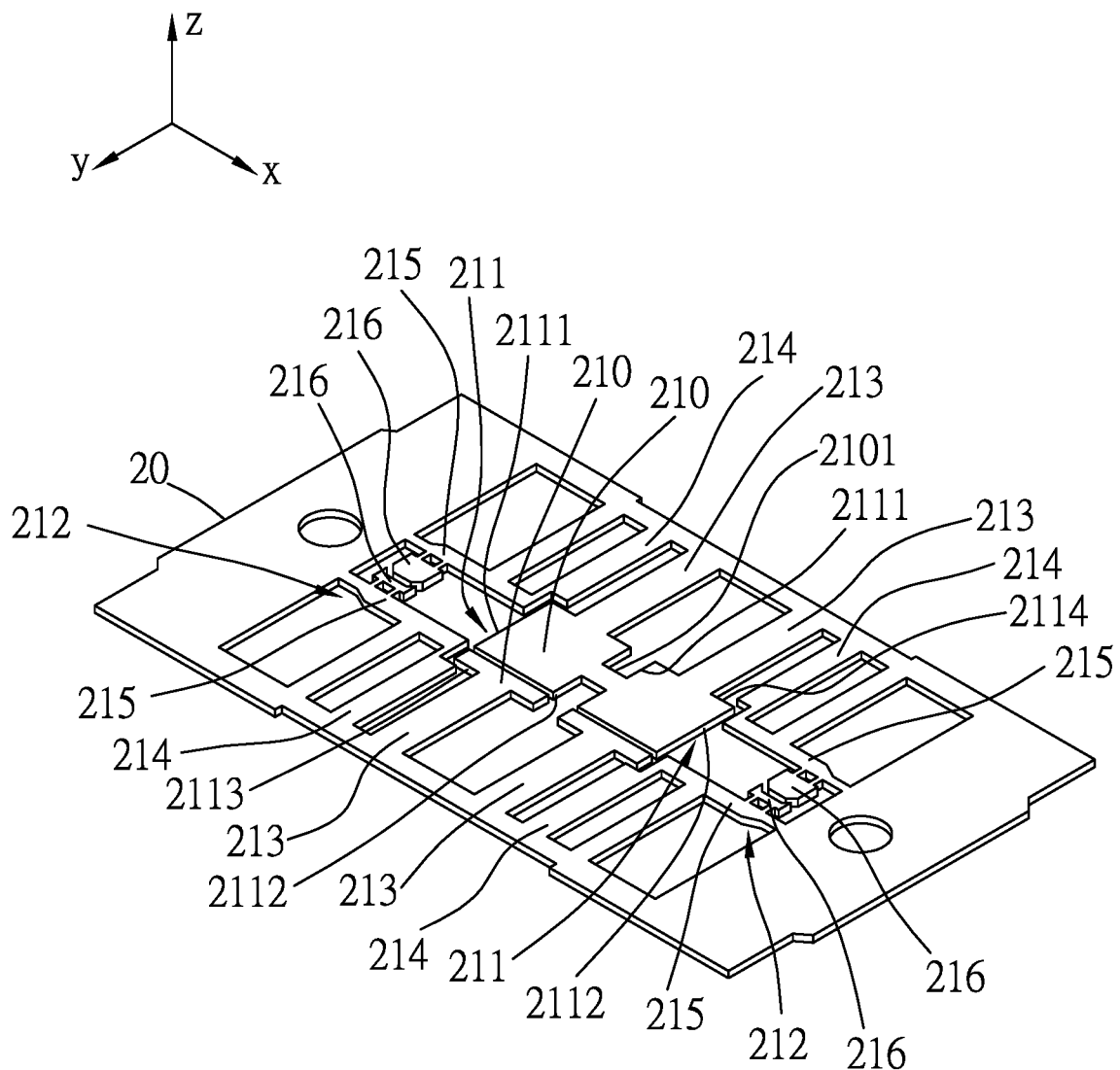
FIG. 6 is a perspective view of a metal plate for forming a modification of the embodiment of the optical sensor module according to the present disclosure.
Figure 7:
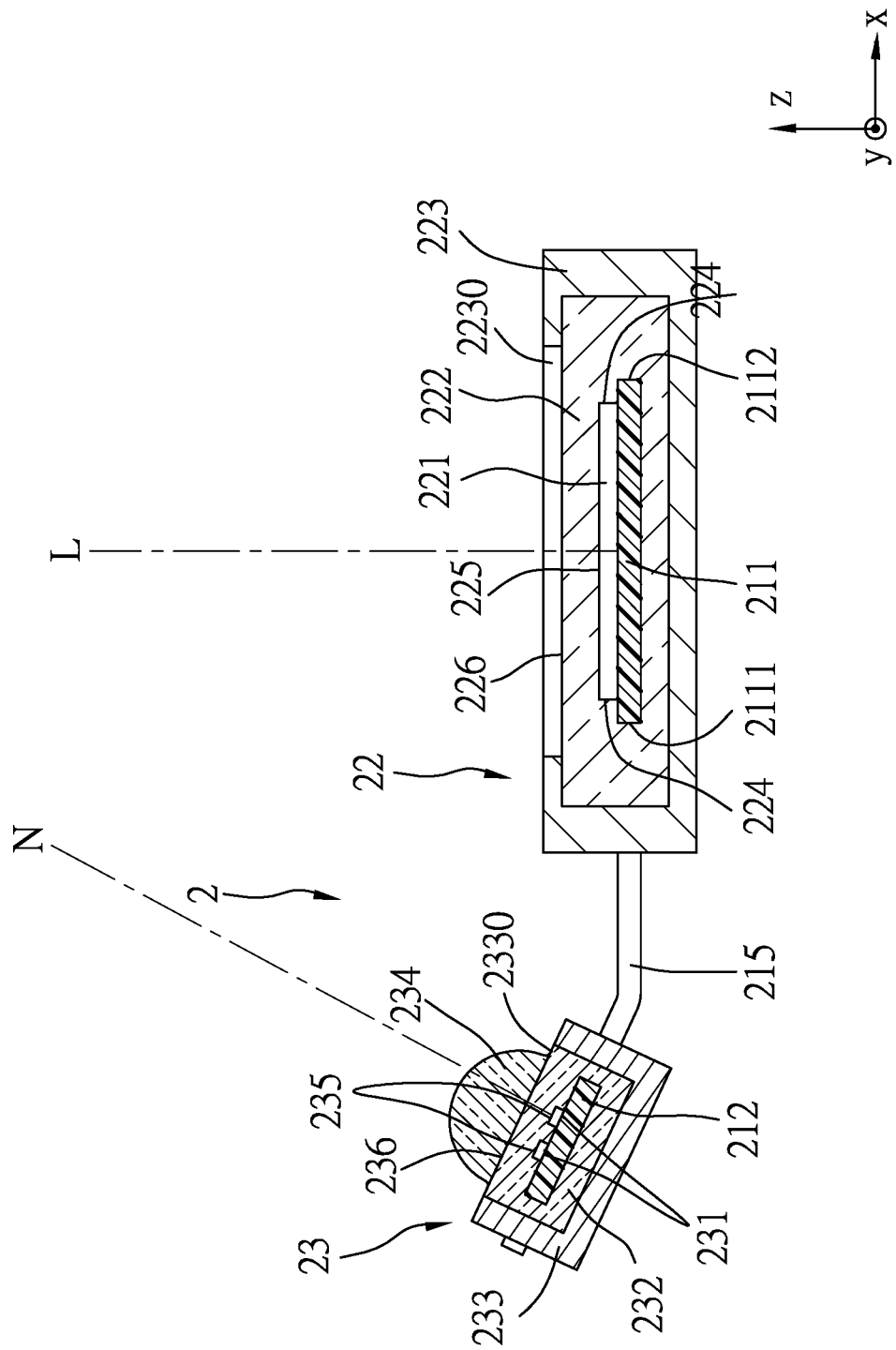
FIG. 7 is a sectional view of the modification of the embodiment.
Figure 8:
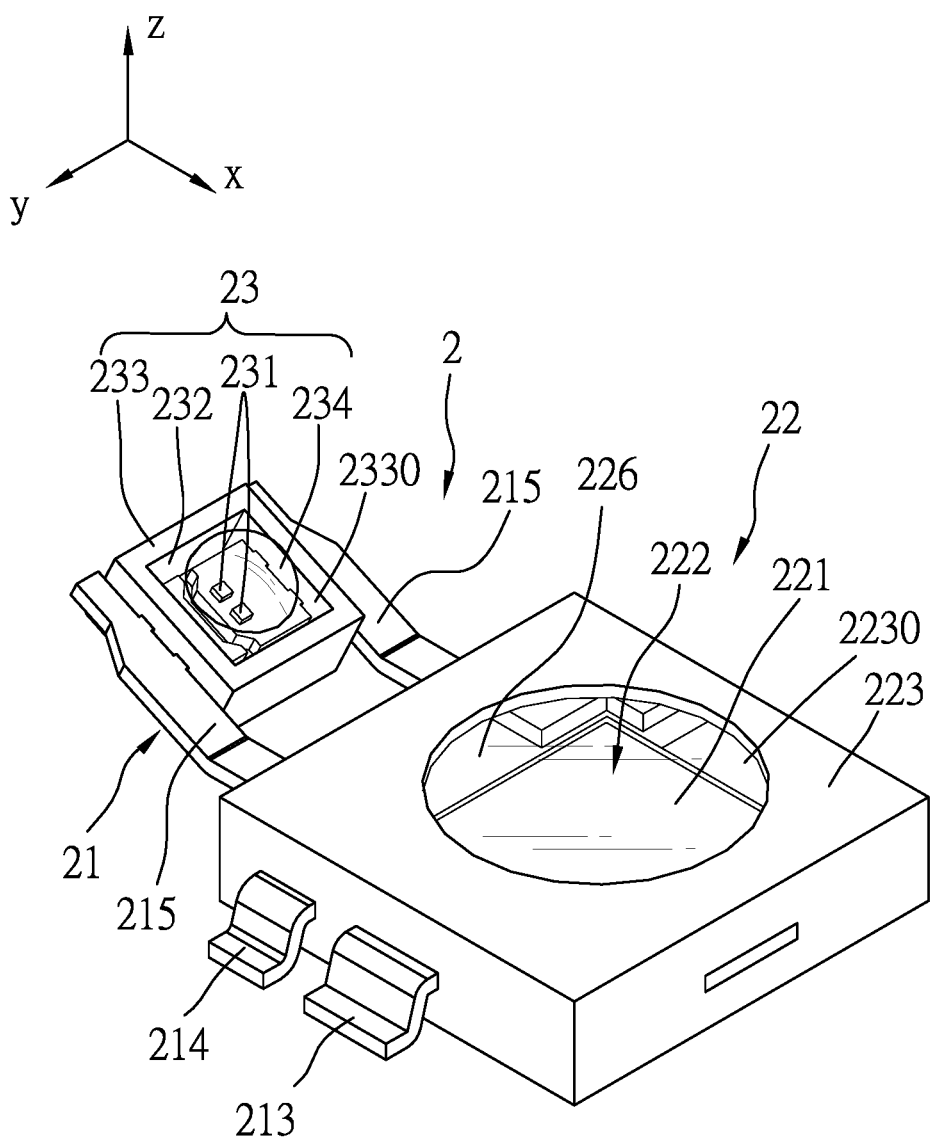
FIG. 8 is a perspective view of the modification of the embodiment.

FIGS. 6 to 8 illustrate a modification of the embodiment of the optical sensor module 2 according to the present disclosure. The optical sensor module 2 includes a light-receiving unit 22, a light-emitting unit 23 disposed near one side of the light-receiving unit 22, and a support unit 21 connecting the light-receiving unit 22 and the light-emitting unit 23. In this modification, the support unit 21 includes a main plate 211 and a single side plate 212. A single copper plate 20 can be formed into at least two support units 21 that are supported and connected to each other via at least one supplement frame 2101 between any two neighboring main plates 211. For each support unit 21, the main plate 211 includes two spaced-apart main portions 210 opposite to and spaced apart from each other in the lengthwise direction (Y).

The spaced-apart main portions 210 cooperatively define the first and second sides 2111, 2112 of the main plate 211 in the lengthwise direction (Y). The supplement frame 2101 extends in the extending direction (X) and connects the first side 2111 of one of the main plates 211 and the second side 2112 of the neighboring one of the main plates 211. The main plate 211 of each of the support units 21 further includes two spaced-apart first leg portions 213 that respectively extend from the third and fourth sides 2113, 2114 in a lengthwise direction (Y) to be away from each other.

The side plate 212 of each of the support units 21 includes two bridge portions 215 that separately extend toward the main plate 211, and two spaced-apart second leg portions 214 that are respectively connected to the bridge portions 215 and that are opposite from each other in the lengthwise direction (Y).

The bridge portions 215 are bendable relative to the main plate 211 in the elevational direction (Z) and the extending direction (X) such that the side plate 212 and the main plate 211 are formable into a three dimensional (3D) structure. Specifically, the bridge portions 215 of the side plate 212 of one of the support units 21 extend toward one of the first and second sides 2111, 2112 of the main plate 211 in the extending direction (X), and are exposed from and inclined relative to the first light-blocking member 223.

The light-emitting unit 23 is exemplified to include two light sources 231 mounted on the side plate 212, a light-transmissible encapsulant 232, a second light-blocking member 233, and a lens 234 disposed on the light-transmissible encapsulant 232.

Each of the light sources 231 has a light-emitting surface 235 located away from the side plate 212. The light-transmissible encapsulant 232 encapsulates the light-emitting sources 231, and has a top surface 236 located away from the light-emitting surfaces 235 of the light sources 231. The second light-blocking member 233 surrounds the light-transmissible encapsulant 232 and the light-emitting sources 231, and has an aperture 2330 registered with the light-emitting surfaces 235 of the light-emitting sources 231. The top surface 236 of the light-transmissible encapsulant 232 is exposed from the aperture 2330 such that the light rays emitted from the light-emitting sources 231 can exit through the top surface 236. The lens 234 is disposed on the top surface 236, thereby enhancing luminous efficiency of the light-emitting sources 231.

To manufacture two optical sensor modules 2, the two support units 21 are separated from each other by removing the supplement frame 2101 in connection therebetween and by cutting the first and second leg portions 213, 214 and the bridge portions 215 of the support units 21 from the single copper plate 20, sequentially or simultaneously.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An optical sensor module, comprising:
   a support unit having a main plate and at least one side plate, said at least one side plate including a plurality of bendable bridge portions and a plurality of body portions respectively connected to said bridge portions, said bridge portions being bent to dispose said body portions laterally displaced from and inclined relative to said main plate;
   a light-receiving unit having a photodetector that is disposed on a top of said main plate and that has a light-receiving surface located away from said main plate, and a first light-blocking member, said photodetector being disposed inside said first light-blocking member; and
   at least one light-emitting unit disposed on at least one of said body portions of said at least one side plate, and having at least one light source that has a light-emitting surface;
   wherein said optical sensor module defines an imaginary line perpendicular to said light-receiving surface, said at least one light source emitting light toward the imaginary line;
   wherein a portion of said first light-blocking member is disposed between said at least one light source and said photodetector; and
   wherein said body portions are disposed outside of said first light-blocking member of said light-receiving unit, said bridge portions projecting outwardly from said first light-blocking member, said body portions thereby connecting respectively with said bridge portions outside of said first light-blocking member, said bridge portions being bent outside of said first light-blocking member to dispose said body portions to be inclined relative to said main plate.

2. The optical sensor module as claimed in claim 1, wherein said support unit includes two of said at least one side plates that are respectively disposed adjacent to two opposite lateral sides of said main plate, and wherein said optical sensor module includes two of said at least one light-emitting units respectively disposed on said side plates.

3. The optical sensor module as claimed in claim 1, wherein said at least one light-emitting unit includes a light-transmissible encapsulant encapsulating said at least one light source, and a second light-blocking member surrounding said light-transmissible encapsulant and said at least one light source, said second light-blocking member having an aperture registered with said light-emitting surface of said at least one light source, said light-transmissible encapsulant having a top surface exposed from said aperture.

4. The optical sensor module as claimed in claim 3, wherein said at least one light-emitting unit includes a lens disposed on said top surface of said light-transmissible encapsulant.

5. The optical sensor module as claimed in claim 1, wherein said light-receiving unit includes a light-transmissible member encapsulating said photodetector, and being surrounded by said first light-blocking member, said first light-blocking member having an opening registered with said light-receiving surface of said photodetector, said light-transmissible member having a top surface exposed from said opening of said first light-blocking member.

6. The optical sensor module as claimed in claim 1, wherein said main plate includes two spaced-apart main portions, said photodetector being disposed on one of said main portions, each said at least one side plate including two of said body portions spaced apart from one another and two of said bridge portions that are respectively connected to said body portions.

7. The optical sensor module as claimed in claim 6, wherein said main plate includes two spaced-apart first leg portions respectively extending from said main portions and exposed outwardly of two opposite ends of said first light-blocking member in a lengthwise direction, each said at least one side plate including two spaced-apart second leg portions respectively connected with said bridge portions and exposed outwardly of said two opposite ends of said first light-blocking member along the lengthwise direction, wherein said first leg portions and said second leg portions are electrically isolated from each other.

8. The optical sensor module as claimed in claim 7, wherein each of said bridge portions of said at least one side plate is formed with a cut-off at an end that a corresponding one of said second leg portions extends from and intersects therewith.

9. The optical sensor module as claimed in claim 1, wherein said photodetector includes two opposite side surfaces, one of said opposite side surfaces being spaced apart from and facing said at least one side plate, said at least one light-emitting unit having a geometric center and defining a normal line normal to said light-emitting surface, and
   $D_2 \tan \theta < D_1/2$, where $D_2$ represents a distance between said light-receiving surface and an outer predetermined reflection surface, $\theta$ represents an included angle between the normal line and the imaginary line, and $D_1$ denotes a distance between said geometric center of said at least one light-emitting unit and one of said opposite side surfaces of said photodetector.

10. The optical sensor module as claimed in claim 1, wherein said at least one light source has a wavelength between 510 nm and 550 nm.

11. The optical sensor module as claimed in claim 1, wherein said at least one light source has a wavelength between 560 nm and 600 nm.

12. A wearable device to be worn by a user for measuring photoplethysmography signals from the user, comprising:
    a housing including a housing body having a transparent cover for contacting with the user's skin, and a wearing member connected to said housing body and configured to be worn by the user;
    a circuit board disposed in said housing body; and
    an optical sensor module mounted on said circuit board and located between said transparent cover and said circuit board, said optical sensor module including:
      a support unit having a main plate and at least one side plate, said at least one side plate including a plurality of bendable bridge portions and a plurality of body portions respectively connected to said bridge portions, said bridge portions being bent to dispose said body portions laterally displaced from and inclined relative to said main plate;
      a light-receiving unit having a photodetector that is disposed on a top of said main plate and that has a light-receiving surface located away from said main plate, and a first light-blocking member, said photodetector being disposed inside said first light-blocking member; and at least one light-emitting unit disposed on at least one of said body portions of said at least one side plate, and having at least one light source that has a light-emitting surface;

wherein said optical sensor module defines an imaginary line perpendicular to said light-receiving surface, said at least one light source emitting light toward the imaginary line;

wherein a portion of said first light-blocking member is disposed between said at least one light source and said photodetector; and wherein said body portions are disposed outside of said first light-blocking member of said light-receiving unit, said bridge portions projecting outwardly from said first light-blocking member, said body portions thereby connecting respectively with said bridge portions outside of said first light-blocking member, said bridge portions being bent outside of said first light-blocking member to dispose said body portions to be inclined relative to said main plate.

13. The wearable device as claimed in claim 12, wherein said photodetector includes two opposite side surfaces, one of said opposite side surfaces being spaced apart from and facing said at least one side plate, said at least one light-emitting unit having a geometric center and defining a normal line normal to said light-emitting surface, and $D_2 \tan \theta < D_1/2$, where $D_2$ represents a distance between said light-receiving surface and said transparent cover, $\theta$ represents an included angle between the normal line and the imaginary line, and $D_1$ denotes a distance between said geometric center of said at least one light-emitting unit and one of said opposite side surfaces of said photodetector.

14. The wearable device as claimed in claim 12, wherein said support unit includes two of said at least one side plates that are respectively disposed adjacent to two opposite lateral sides of said main plate, and wherein said optical sensor module includes two of said at least one light-emitting units respectively disposed on said side plates.

15. The wearable device as claimed in claim 12, wherein said at least one light-emitting unit includes a light-transmissible encapsulant encapsulating said at least one light source, and a second light-blocking member surrounding said light-transmissible encapsulant and said at least one light source, said second light-blocking member having an aperture registered with said light-emitting surface of said at least one light source, said light-transmissible encapsulant having a top surface exposed from said aperture.

16. The wearable device as claimed in claim 15, wherein said at least one light-emitting unit includes a lens disposed on said top surface of said light-transmissible encapsulant.

17. The wearable device as claimed in claim 12, wherein said light-receiving unit includes a light-transmissible member encapsulating said photodetector, and being surrounded by said first light-blocking member, said first light-blocking member having an opening registered with said light-receiving surface of said photodetector, said light-transmissible member having a top surface exposed from said opening of said first light-blocking member.

18. The wearable device as claimed in claim 12, wherein said main plate includes two spaced-apart main portions, said photodetector being disposed on one of said main portions, each said at least one side plate having two of said body portions spaced apart from one another and two of said bridge portions that are respectively connected to said body portions.

19. The optical sensor module as claimed in claim 18, wherein said main plate includes two spaced-apart first leg portions respectively extending from said main portions and exposed outwardly of two opposite ends of said first light-blocking member in a lengthwise direction, each said at least one side plate including two spaced-apart second leg portions respectively connected with said bridge portions and exposed outwardly of said two opposite ends of said first light-blocking member along the lengthwise direction, wherein said first leg portions and said second leg portions are electrically isolated from each other.

* * * * *